US00PP25349P3

(12) United States Plant Patent
Bak et al.

(10) Patent No.: US PP25,349 P3
(45) Date of Patent: Mar. 17, 2015

(54) ***MEDINILLA* HYBRID PLANT NAMED 'MAGIC'**

(50) Latin Name: ***Medinilla* sp.**
Varietal Denomination: Magic

(71) Applicant: Corn.Bak B.V., Assendelft (NL)

(72) Inventors: Elly Bak, Rijsenhout (NL); Nicolaas D. M. Steur, Oude Niedorp (NL)

(73) Assignee: Corn.Bak B.V., Assendelft (NL)

( * ) Notice: Subject to any disclaimer, the term of this patent is extended or adjusted under 35 U.S.C. 154(b) by 129 days.

(21) Appl. No.: 13/694,587

(22) Filed: Dec. 14, 2012

(65) Prior Publication Data

US 2014/0173795 P1 Jun. 19, 2014

(51) Int. Cl.
*A01H 5/00* (2006.01)

(52) U.S. Cl.
USPC ..... Plt./263.1

(58) Field of Classification Search
CPC ..... A01H 5/00; A01H 5/02
USPC ..... Plt./263.1, 226
See application file for complete search history.

(56) References Cited

PUBLICATIONS

Printout of application information from Community Plant Variety Office (CPVO) website for corresponding CPVO application No. 2011/2822 filed Nov. 24, 2011 (1 page) (http://www.cpvoextranet.cpvo.europa.eu).

Printout of application information for Canadian Plant Breeders' Rights application No. 12-7764 filed Oct. 12, 2012, published in Plant Varieties Journal No. 86, Jan. 31, 2013 (1 page) (www.inspection.gc.ca/plants/plant-breeders-rights/plant-varieties-journal).

*Primary Examiner* — Susan McCormick Ewoldt
(74) *Attorney, Agent, or Firm* — Foley & Lardner LLP

(57) ABSTRACT

A new and distinct *Medinilla* sp. plant named 'MAGIC', characterized by a erect shrub plant, measuring about 25-30 cm in total height (when first flowering) and about 30 cm in diameter; green colored leaves, measuring about 12 cm in length and about 3.5-4.5 cm in width; and pendulous panicles, measuring about 20 cm in length and about 10 cm in diameter, with red (RHS 53C) flowers.

2 Drawing Sheets

Latin name of the genus and species of the plant claimed: *Medinilla* sp.

Variety denomination: 'MAGIC'.

BACKGROUND OF THE INVENTION

The present invention relates to a new and distinct hybrid cultivar of *Medinilla* plant, botanically known as *Medinilla* sp., hereinafter referred to by the cultivar name 'MAGIC'. The genus of *Medinilla* belongs to the Melastomataceae family. The new *Medinilla* 'MAGIC' is a product of a planned breeding program conducted by the inventors, Elly Bak and Nicolaas D. M. Steur, in Assendelft, The Netherlands. The objective of the breeding program is to develop a new *Medinilla* variety with good growing habit and attractive inflorescence. The new *Medinilla* 'MAGIC' originated from a cross made in a controlled breeding program by the inventors in 2008 in Assendelft, The Netherlands. The female or seed parent is the *Medinilla* selection designated '84068295' (unpatented), and the male or pollen parent is the *Medinilla* selection designated '84064514' (unpatented). 'MAGIC' was discovered and selected by the inventors in 2010, as a single flowering plant within the progeny of the stated cross in a controlled environment in Assendelft, The Netherlands.

Asexual reproduction of the new *Medinilla* hybrid 'MAGIC' performed by vegetative means by cuttings was first performed in 2010, in Assendelft, The Netherlands. The first 'MAGIC' plants propagated through the use of cuttings flowered in 2011, in Assendelft, The Netherlands, and have demonstrated that the combination of characteristics as herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be unique characteristics of 'MAGIC' which in combination distinguish this *Medinilla* hybrid as a new and distinct cultivar:

1. Solid growth habit;
2. Erect shrub plant, measuring about 25-30 cm in height (above the pot when first flowering);
3. Green colored leaves, measuring about 12 cm in length and about 4 cm in width;
4. Pendulous panicles with red (RHS 53C) colored flowers;

Of the many commercial cultivars known to the present inventors, the most similar in comparison to the new *Medinilla* variety 'MAGIC' is the *Medinilla* variety 'BELLA' (Patented, U.S. Plant Pat. No. 23,635). Plants of the new *Medinilla* 'MAGIC' differ from plants of *Medinilla* 'BELLA' primarily in leaf size, bract size, and inflorescence color. Plants of 'MAGIC' have smaller leaves and bracts than plants of 'BELLA'. Additionally, plants of 'MAGIC' have more inflorescences.

When the new *Medinilla* variety 'MAGIC' is compared to the parent varieties, the female parent '84068295' has larger leaves and larger inflorescences than 'MAGIC'. The male parent '84064514' has a wider plant diameter (spread) than 'MAGIC'.

BRIEF DESCRIPTION OF THE PHOTOGRAPHS

The accompanying photographs illustrate the overall appearance of the new *Medinilla* 'MAGIC' showing the colors as true as is reasonably possible with colored reproductions of this type. Colors in the photographs may differ slightly from the color values cited in the detailed botanical description which accurately describes the color of 'MAGIC'.

DETAILED BOTANICAL DESCRIPTION

Figure 1:
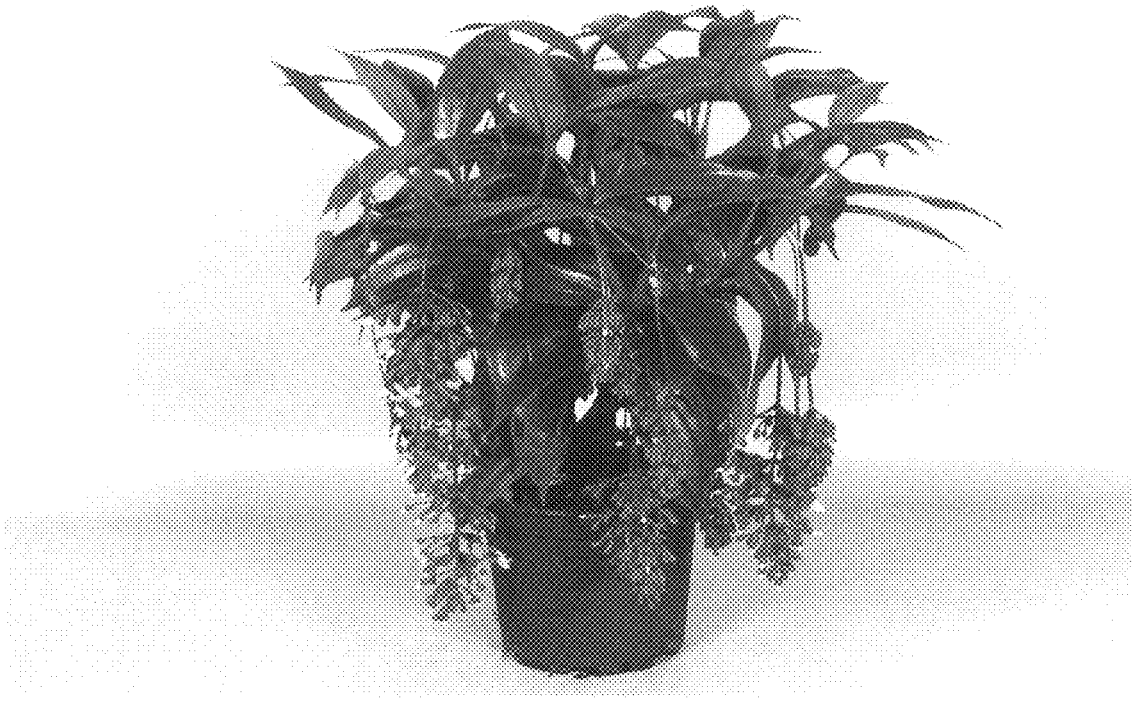
FIG. 1 shows a side view perspective of a typical potted flowering plant of 'MAGIC' at about 50 weeks from potting.
Figure 2:
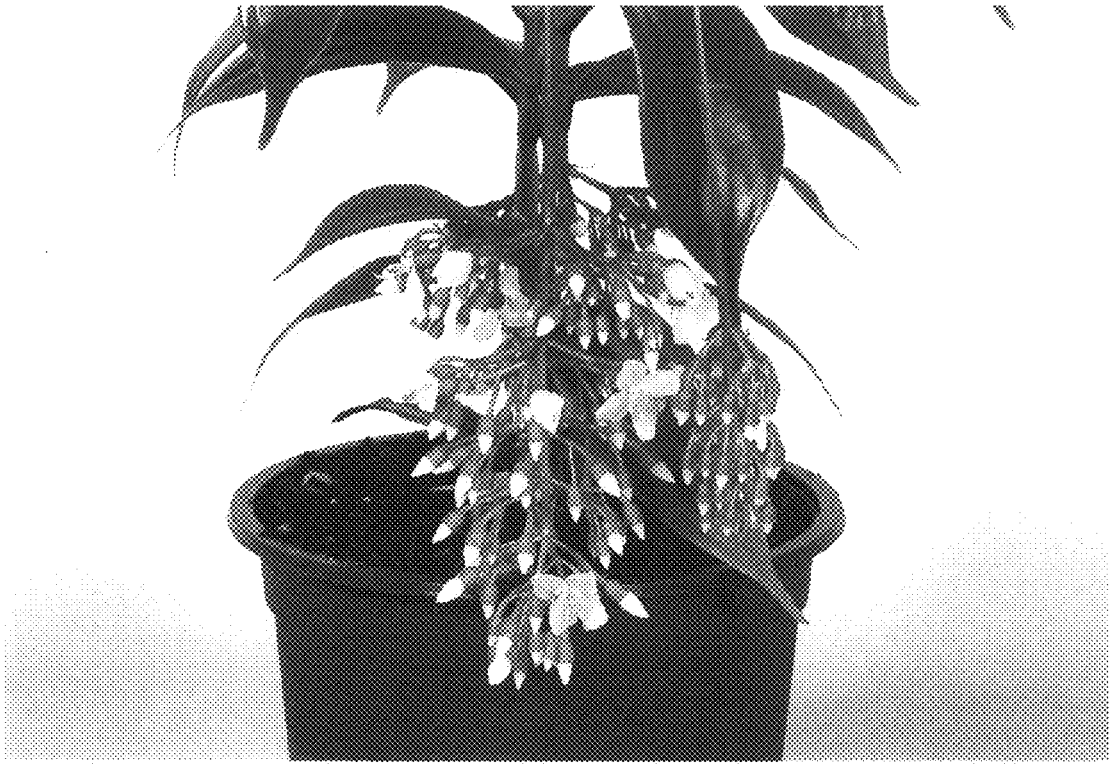
FIG. 2 shows a close up view of a typical panicle of 'MAGIC' on a flowering plant at about 50 weeks from potting.

'MAGIC' has not been observed under all possible environmental conditions. The phenotype of the new cultivar may vary with variations in environment such as temperature, light intensity, day length, fertilizers and humidity without any change in the genotype of the plant. The aforementioned photograph, together with the following observations, measurements and values describe the new *Medinilla* 'MAGIC' as grown in a greenhouse in Assendelft, The Netherlands, under conditions which closely approximate those generally used in commercial practice.

Color references are made to The Royal Horticultural Society Colour Chart (R.H.S.), 2001 Edition, except where general colors of ordinary significance are used. Color values were taken under daylight conditions in a greenhouse in Assendelft, The Netherlands. The age of the plants of 'MAGIC' described is about 50 weeks from potting.

Classification: Botanical: *Medinilla* sp.

Parentage: Female Parent: *Medinilla* selection designated '84068295' (unpatented). Male Parent: *Medinilla* selection designated '84064514' (unpatented).

Propagation: Cuttings.

Plant:

*General appearance and form*.—Height: About 25-30 cm. Diameter: About 30 cm. Shape: Erect shrub. Growth habit: stem. Plant Vigor: good. Flowering Season: from April until October. Cold Tolerance: frost tender, temperatures below 5C may damage plants.

*Fragrance*.—None.

*Stem*.—Shape: Square, winged. Diameter: About 10 mm. Width of wings: about 3 mm. Length of internodes: about 3.5 to 6 mm. Color: Green, RHS 143A with lignified parts colored Grey-Brown, RHS 199B.

Foliage:

*Quantity*.—About 40.

*Arrangement*.—Opposite.

*Attachment*.—Petiolate.

*Size*.—Length: About 12 cm. Width: About 3.5-4.5 cm.

*Overall shape*.—Elliptical.

*Apex shape*.—Cuspidate.

*Base shape*.—Acute.

*Margin*.—Slightly undulate.

*Texture*.—Smooth.

*Color*.—Leaf color can vary somewhat depending on growing conditions. Upper Surface: Glossy green, ranges between RHS 137A and RHS 139A. Lower Surface: Green, ranges between RHS 137C and RHS 143A.

*Venation*.—Present; slightly sunken below leaf surface. Pattern: parallel. Color: Upper side: Yellow Green, RHS 144B. Lower side: Red-purple, RHS 60A.

Inflorescence:

*Shape*.—Pendulous panicles.

*Amount*.—About 20 (depending on the size of the plant).

*Flower buds*.—Length: About 10 mm. Diameter: About 6 mm. Color: Red-purple, RHS 60B.

*Size*.—Length: About 20 cm. Width: About 10 cm.

*Color*.—Red, closest to RHS 53C.

*Corolla*.—Number: about 120 per panicle.

*Petals*.—Number: 4 or 5 per flower. Length: 10 mm. Width: 7 mm. Overall Shape: obovate, asymmetrical. Apex Shape: obtuse. Color: Upper surface: white, closest to RHS 155D. Lower surface: white, closest to RHS 155D.

*Sepals*.—Growth together, enclosing the ovary. Color: red, closest to RHS 53C.

*Bracts*.—Quantity: 4 per crown. Arrangement: verticillate. Color: Green RHS 143B, with some red-purple, RHS 59A.

*Size*.—Length: about 1-13 mm. Width: less than 1-2 mm.

*Overall shape*.—Elliptical.

*Peduncle*.—Length: about 18-28 cm. Diameter: about 2 mm. Color: Yellow-Green RHS 144B at the base, changing to Red-Purple RHS 59A.

*Pedicel*.—Length: about 4 mm to 12 mm (at the top). Diameter: about 2 mm. Color: Red-purple, RHS 64B.

Reproductive organs:

*Androecium*.—Stamen: Number: 8-10 per flower. Length: 7 mm. Diameter: less than 1 mm. Color: light yellow, with a white base (too small to qualify RHS value). Anther: Length: 8 mm. Color: violet, closest to RHS 87B, with a yellow base (too small to qualify RHS value). Pollen: not visible.

*Gynoecium*.—Pistil: Number: 1 per flower. Length: 12 mm. Stigma: Width: less than 1 mm. Color: white, too small to qualify RHS value. Style: Length: 17 mm. Color: white, closest to RHS 155B. Ovary: Shape: round. Position: inferior. Length: 3 mm. Diameter: 3 mm. Color: white, closest to RHS 155C.

Seeds:

*Amount*.—Numerous.

*Shape*.—Obovate.

*Texture*.—Glabrous.

*Size*.—Less than 1 mm.

Fruit:

*Type*.—Berry.

*Shape*.—Round.

*Texture*.—Smooth.

*Size*.—0.5-1 cm.

Disease/pest resistance: No observations made.

Disease/pest susceptibility: No observations made.

What is claimed is:

1. A new and distinct *Medinilla* plant named 'MAGIC', substantially as illustrated and described herein.

* * * * *